United States Patent [19]

Büchi et al.

[11] Patent Number: 4,677,233

[45] Date of Patent: Jun. 30, 1987

[54] PROCESS FOR THE PREPARATION OF (±)-3A-6,6,9A-TETRAMETHYLPERHYDRONAPHTO[2,1-B]FURAN

[75] Inventors: George H. Büchi; Hans Wüest, both of Cambridge, Mass.

[73] Assignee: Firmenich SA, Geneva, Switzerland

[21] Appl. No.: 877,634

[22] Filed: Jun. 23, 1986

Related U.S. Application Data

[62] Division of Ser. No. 638,791, Aug. 8, 1984, Pat. No. 4,613,710.

[51] Int. Cl.$^4$ ............................................. C07C 35/23
[52] U.S. Cl. .................................................... 568/819
[58] Field of Search ......................................... 568/819

[56] References Cited

U.S. PATENT DOCUMENTS 4,296,038  10/1981  Ho et al. ............................. 568/819
4,613,710  9/1986  Buchi et al. ......................... 568/819

OTHER PUBLICATIONS

Sousa et al, "J. Org. Chem.", vol. 25, pp. 108–111 (1960).
Sibiertseva et al., "Chemical Abstracts", vol. 93, p 114751w (1980).

*Primary Examiner*—Werren B. Lone
*Attorney, Agent, or Firm*—Pennie & Edmonds

[57] ABSTRACT

3a,6,6,9a-Tetramethylperhydronaphto[2,1-b]furan, a typical ambergris perfume ingredient is prepared via a novel process from 1β-(2-hydroxyethyl)-perhydro-2,5,5,8aβ-tetramethyl-2β-trans-napthalenol by cyclization with an acidic cyclization agent in the presence of nitromethane.

1 Claim, No Drawings

PROCESS FOR THE PREPARATION OF (±)-3A-6,6,9A-TETRAMETHYLPERHYDRONAPHTO[2,1-B]FURAN

This is a division of application Ser. No. 638,791, filed Aug. 8, 1984, now U.S. Pat. No. 4,613,710.

SUMMARY OF THE INVENTION

The present invention relates to a process for the preparation of (±)-3a,6,6,9a-tetramethylperphydronaphto[2,1-b]furan, a tricyclic decalinic ether of formula

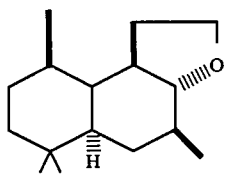

which process comprises the step of cyclising 1β-(2-hydroxyethyl)-perhydro-2,5,5,8aβ-tetramethyl-2β-trans-naphthalenol by means of an acidic cyclisation agent in the presence of nitromethane.

The invention relates further to the following novel intermediates in the process for obtaining said naphtalenol starting from known methyl perhydro-5,5,8aβ-trimethyl-2-oxo-1β-trans-naphtalenecarboxylate:

methyl 2-allyloxy-3,4,4a,5,6,7,8,8a-octahydro-5,5,8a-trimethyl-1-trans-naphthalenecarboxylate,
methyl 1-allyl-perhydro-5,5,8a-trimethyl-1-trans-naphthalenecarboxylate,
1β-allyl-perhydro-5,5,8aβ-trimethyl-2-trans-naphthalenone, and
1β-allyl-perhydro-2,5,5,8aβ-tetramethyl-2β-trans-naphthalenol.

BACKGROUND OF THE INVENTION

A mixture containing 3a,6,6,9a-tetramethylperhydronaphto[2,1-b]furan of formula

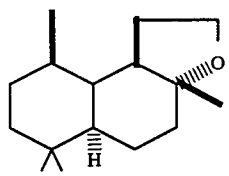

together with minor amounts of its diastereoisomer of formula

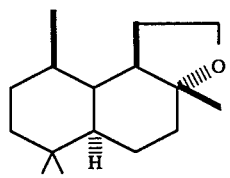

has been commercialized under the form of a perfume speciality base for over twenty years (FIXATEUR 404 ®, origin: Firmenich SA, Geneva, Switzerland). The former of the above compounds is better known by its tradename AMBROX (registered trademark of Firmenich SA) whereas the latter is defined by analogy as "iso-AMBROX".

Owing to its typical ambergris character of special radiance, AMBROX has become a perfume ingredient of great usefulness.

Since its discovery [see Helv. Chim. Acta 33, 1251 (1950)], numerous syntheses have been proposed by different research teams. These are generally based on oxidative degradation of diterpenes such as (−)-sclareol or (+)-manool, or employ ambreine as starting material [G. Ohloff in Fragrance Chemistry, ed. Ernst T. Theimer, p. 545, Academic Press (1982)]. These products are all of natural origin and consequently their availability and their quality depend on weather conditions as well as on variable socio-political situations. Yields for their extraction from the natural sources are low and their market price renders their utilization uneconomical. Such a synthetic approach can be illustrated by means of the following simplified reaction pathway:

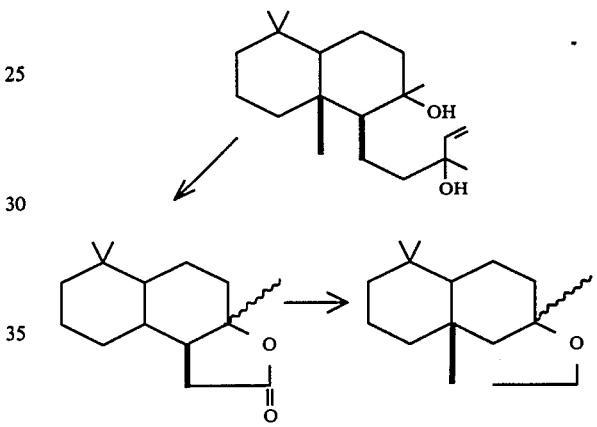

Thus, AMBROX, in spite of its exceptional fragrance properties, has remained so far a product of relatively limited use. The present invention brings a novel and original solution to the challenging problem set by its preparation. By using synthetic raw materials, the process of the invention overcomes the drawbacks of the known methods and constitutes therefore a useful economical alternative from the industrial viewpoint.

THE INVENTION

The critical step of the invention process consists in the cyclisation of a diol of formula

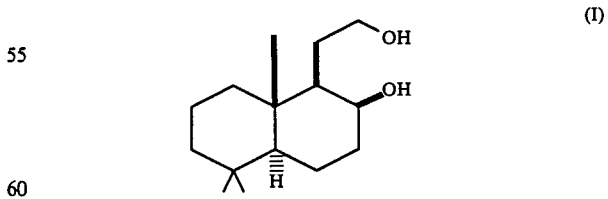

(I)

by means of an acidic cyclisation agent in the presence of nitromethane. Suitable acidic cyclisation agents include mineral protonic acids, carboxylic acids, acidic diatomaceous earth or acidic cationic resins. Derivatives of sulfonic acid can also be employed and to this effect p-toluenesulfonic acid is preferred. By analogy with a known process [see Sibiertseva et al., Chem.

Abstr. 93, 114751 (1980)], one might have expected that under these reaction conditions the cyclisation would have resulted in the formation of iso-AMBROX. In fact, the cyclisation of diol (I) with p-toluenesulfonic acid according to Sibiertseva occurs without inversion of the

group.

Iso-AMBROX thus formed, though possessing the typical qualitative characters of AMBROX itself, differs from it insofar as its perception level is concerned as shown in following table.

| Compound | Formula | Perception Level (ppb)* |
|---|---|---|
| AMBROX |  | 0,4 |
| iso-AMBROX |  | 28 |

*parts per billion

From the above figures, it follows that the product obtained by the process of the invention possesses an odor power well superior to that of the isomeric compound obtained by the cyclisation described by Sibiertseva. The action of nitromethane in the above defined cyclisation promotes in the acidic reaction medium an epimerization of asymmetric group

thus driving the reaction toward the formation of the desired isomer. Such an action is surprising and totally unexpected.

We have noticed that the essential feature of nitromethane is to reduce the double bond formation subsequent to the dihydration of diol (I) according to the following reaction:

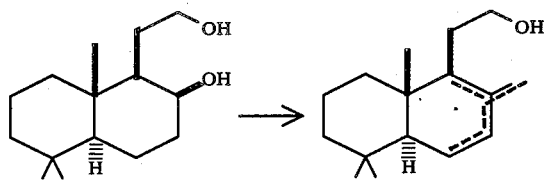

The reaction is carried out at a temperature higher than room temperature, lower though than the boiling point, at atmospheric pressure, of nitromethane. Typically, the chosen temperature is of between 50° and 90° C., preferably of between 75° and 85° C.

According to a preferred mode, the cyclisation is effected by heating at the chosen temperature the mixture consisting of diol (I), the acidic cyclisation agent and nitromethane.

Diol of formula (I), used as starting material in the above described process, is a known compound which can be obtained starting from a bicyclic carbinol of formula

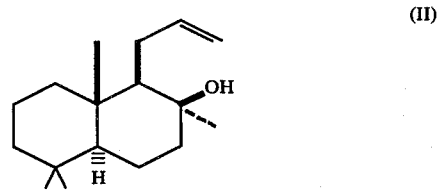

via ozonization followed by reduction by means, for example, of an alkali metal borohydride.

The following reaction scheme illustrates the process for the preparation of said diol (I).

Scheme

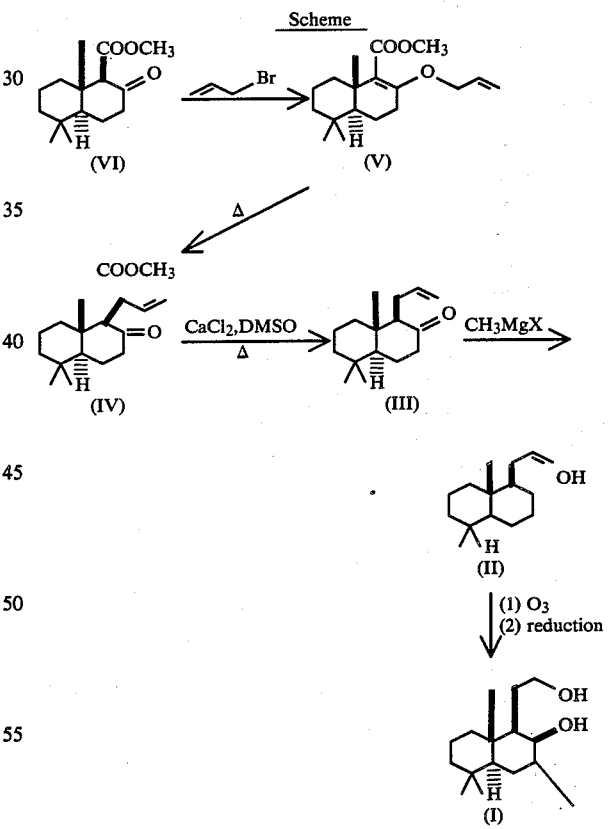

X = halogen
DMSO = dimethylsulfoxide

Intermediates (II) to (V) are novel chemical entities whereas keto-ester (VI) has been described by R. W. Skeean et al. [Tetrahedron Letters 525–8 (1976)] and it can be readily obtained, as indicated by the authors, from geranyl bromide or β-cyclogeranyl bromide.

A preferred embodiment of the process of the invention is described in the following example wherein temperatures are indicated in degreess centigrade and the abbreviations have the meaning common in the art.

EXAMPLE

A.

Methyl 1-allyl-perhydro-5,5,8aβ-trimethyl-2-oxo-1β-trans-naphthalenecarboxylate

Into a 1 l-flask was placed a suspension of 1.2 g (5 mM) of sodium hydride in 70 ml of dimethylformamide. A solution of 12.27 g (48.7 mM) of methyl perhydro-5,5,8aβ-trimethyl-2-oxo-1β-trans-naphthalenecarboxylate in 30 ml of dimethylformamide was added at 5°–10°, then the stirred mixture was allowed to warm up to 20°. After 30 min, it was cooled to 0° and 5.2 ml (60 mM) of allyl bromide was added. The mixture was stirred overnight at room temperature, poured into cold water and extracted with ether. Drying over Na$_2$SO$_4$ and evaporation left 14.1 g of crude methyl 2-allyloxy-3,4,4a,5,6,7,8-,8a-octahydro-5,5,8a-trimethyl-1-trans-naphthalenecarboxylate IR (CHCl$_3$): 1710, 1680 cm$^{-1}$;

NMR (60 MHz, CCl$_4$): 0.85 (3H, s); 0.9 (3H, s); 1.15 (3H, s); 1.02–2.3 (11H, m); 3.6 (3H, s); 4.1 (2H, d, J=6 Hz); 4.8–6.1 (3H, m) δ ppm;

14.1 G of the product thus obtained in 80 ml of xylene were heated at reflux for 3.5 h. The solvent was removed in vacuo and the remaining oil dissolved in 40 ml of hexane was allowed to crystallize at −20° yielding 8.85 g (yield 62%) of the desired product.

A sample was recrystallized from ethyl acetate; m.p. 100°–101°.

IR (CHCl$_3$): 1740, 1705, 1630, 970 and 920 cm$^{-1}$;

NMR (60 MHz; CCl$_4$): 0.95 (3H, s); 1.0 (3H, s); 1.05 (3H, s); 0.8–3.2 (13H, m); 3.6 (3H, s); 4.7–5.8 (3H, m) δ ppm.

B.

1β-Allyl-perhydro-5,5,8aβ-trimethyl-2-trans-naphthalenone

A stirred mixture of 7.30 g (25 mM) of methyl 1-allyl-perhydro-5,5,8aβ-trimethyl-2-oxo-1β-trans-naphthalenecarboxylate, 9.4 g (62 mM) of calcium chloride dihydrate, and 90 ml of dimethylsulfoxide was heated at reflux for 75 min.

It was poured into water, extracted with ether, dried over Na$_2$SO$_4$ and evaporated. Distillation of the remaining oil gave 5.39 g of a product having b.p. 100°–115°/0.07 Torr. Glc (CARBOWAX column) indicated a mixture of 82% of 1β-allyl-perhydro-5,5,8aβ-trimethyl-2-trans-naphthalenone and 13% of starting material. Separation was achieved by silica gel chromatography using hexane+2% ethyl acetate.

IR (CHCl$_3$): 1700, 1630, 990 and 910 cm$^{-1}$;

NMR (60 MHz; CCl$_4$): 0.7 (3H, s); 0.85 (3H, s); 0.95 (3H, s); 1.1–2.6 (14H, m); 4.6–5.0 (2H, m); 5.1–6.0 (1H, m) δ ppm.

C.

1β-Allyl-perhydro-2,5,5,8aβ-tetramethyl-2β-trans-naphthalenol 2.34 G (10 mM) of the ketone obtained according to paragraph B above in 5 ml of ether was added to the Grignard reagent prepared from 0.36 g (15 mg-atoms) of magnesium and 0.9 ml (15 mM) of iodomethane in 20 ml of ether. The mixture was heated at reflux for 30 min, then it was decomposed with aq. ammonium chloride solution and extracted with ether. Drying over Na$_2$SO$_4$, evaporation, and distillation of the residue afforded 2.47 g (98%) of the desired carbinol, b.p. 105°/0.1 Torr.

IR (CHCl$_3$): 3600, 1630 and 910 cm$^{-1}$;

NMR (60 MHz; CCl$_4$): 0.85 (6H, s); 0.9 (3H, s); 1.05 (3H, s); 0.7–2.2 (15H, m); 4.6–5.0 (2H, m); 5.2–5.9 (1H, m) δ ppm.

D.

1β-(2-Hydroxyethyl)-perhydro-2,5,5,8aβ-tetramethyl-2β-trans-naphthalenol

A solution of 2.47 g (9.9 mM) of the carbinol obtained according to paragraph C above, in 60 ml of methanol was ozonized at −20° to −30°. It was then cooled to −60°, 1 g of sodium borohydride was added, and the stirred mixture was allowed to warm up to room temperature.

Most of the methanol was removed in vacuo, water was added, and the mixture was extracted with ether. Evaporation left a residue which was crystallized from ethyl acetate to afford 1.55 g (62%) of the desired product; m.p. 168°–170°.

IR (CHCl$_3$): 3600 and 3450 cm$^{-1}$;

NMR (250 MHz; CDCl$_3$): 0.83 (3H, s); 0.87 (3H, s); 0.98 (3H, s); 1.14 (3H, s); 0.8–1.8 (16H, m); 3.57–3.66 (2H, m) δ ppm.

E.

(±)-AMBROX

A stirred mixture of 640 mg (2.5 mM) of the product obtained according to paragraph D above, 20 mg of p-toluenesulfonic acid, and 50 ml of nitromethane was heated at 80° for 75 min. It was diluted with ether, washed with a sodium bicarbonate solution, dried over Na$_2$SO$_4$ and evaporated. The remaining oil was chromatographed on silica gel. Hexane+2% ethyl acetate eluted 446 mg (75%) of pure racemic AMBROX.

What we claim is:

1. 1β-Allyl-perhydro-2,5,5,8aβ-tetramethyl-2β-trans-naphthalenol.

* * * * *

UNITED STATES PATENT AND TRADEMARK OFFICE
CERTIFICATE OF CORRECTION

PATENT NO. : 4,677,233

DATED : June 30, 1987

INVENTOR(S) : George H. Buchi and Hans Wuest

It is certified that error appears in the above-identified patent and that said Letters Patent is hereby corrected as shown below:

Column 1, lines 15-20, change 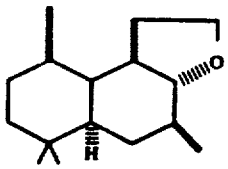 to 

Column 1, lines 45-52, change 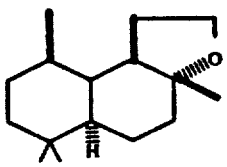 to 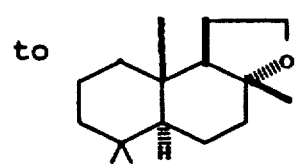

Column 1, lines 55-63, change 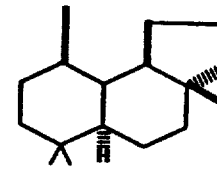 to 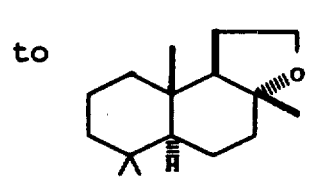

Column 2, lines 30-39, change 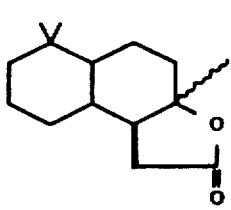

to 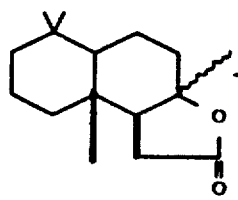 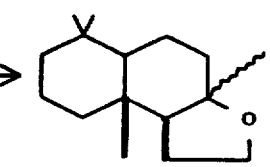

UNITED STATES PATENT AND TRADEMARK OFFICE
CERTIFICATE OF CORRECTION

PATENT NO. : 4,677,233

DATED : June 30, 1987

INVENTOR(S) : George H. Buchi and Hans Wuest

It is certified that error appears in the above-identified patent and that said Letters Patent is hereby corrected as shown below:

Column 2, lines 55-60, change 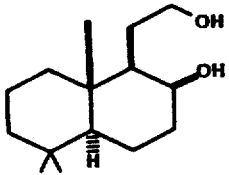 to 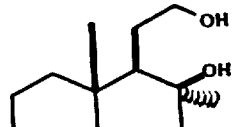

Column 3, lines 22-27, change 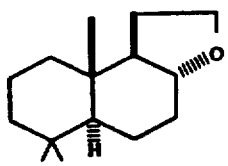 to 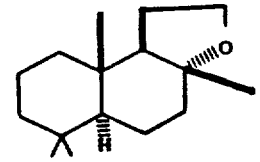

Column 3, lines 59-66, change 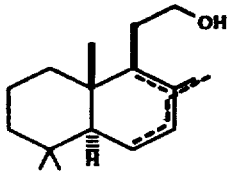 to 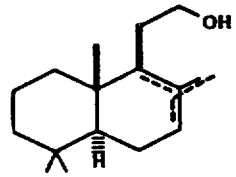

UNITED STATES PATENT AND TRADEMARK OFFICE
CERTIFICATE OF CORRECTION

PATENT NO. : 4,677,233

DATED : June 30, 1987

INVENTOR(S) : George H. Buchi and Hans Wuest

It is certified that error appears in the above-identified patent and that said Letters Patent is hereby corrected as shown below:

Column 4, lines 37-60, change

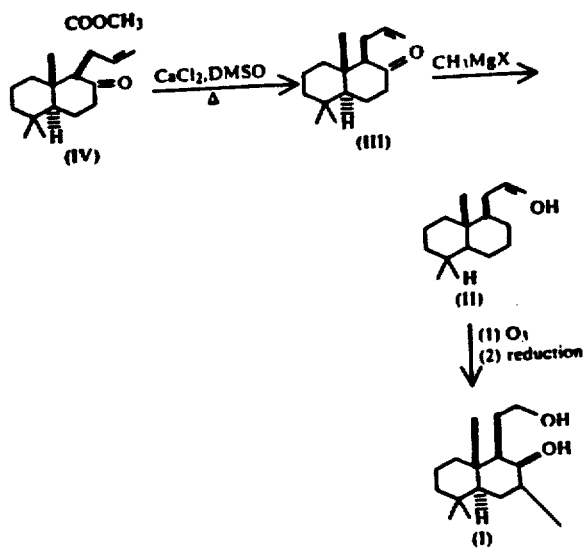

UNITED STATES PATENT AND TRADEMARK OFFICE
CERTIFICATE OF CORRECTION

PATENT NO. : 4,677,233

DATED : June 30, 1987

INVENTOR(S) : George H. Buchi and Hans Wuest

It is certified that error appears in the above-identified patent and that said Letters Patent is hereby corrected as shown below:

to
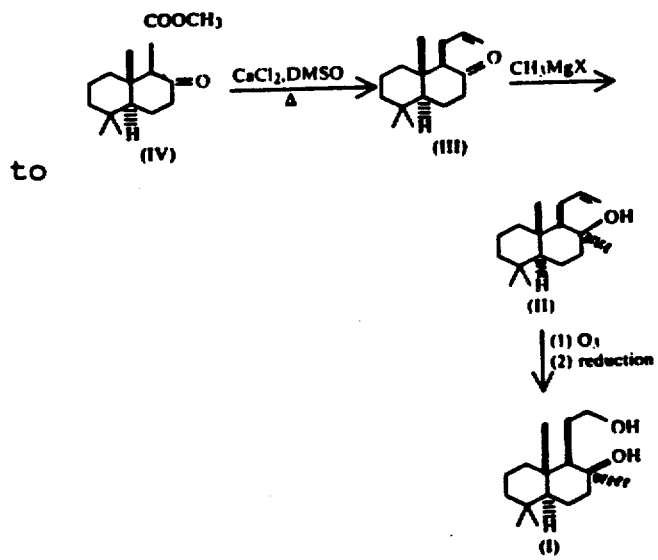

Signed and Sealed this

Sixteenth Day of February, 1988

Attest:

DONALD J. QUIGG

Attesting Officer

Commissioner of Patents and Trademarks